Figure 1:
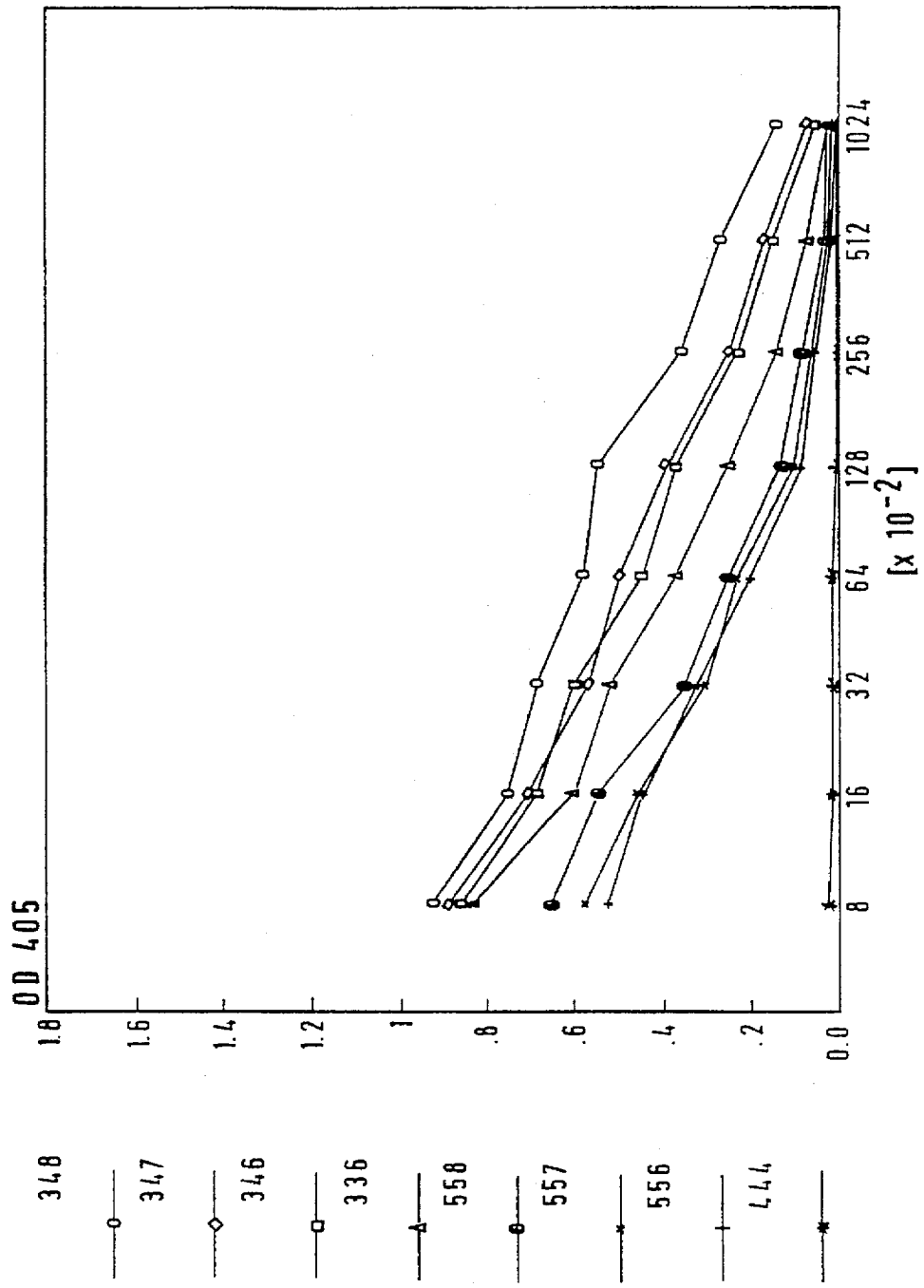

United States Patent [19]

Fibi et al.

[11] Patent Number: 5,712,370
[45] Date of Patent: Jan. 27, 1998

[54] ERYTHROPOIETIN (EPO) PEPTIDES AND ANTIBODIES DIRECTED AGAINST THESE

[75] Inventors: Mathias Fibi, Marburg; Werner Stüber, Lahntal, both of Germany

[73] Assignee: Behringwerke Aktiengesellschaft, Marburg, Germany

[21] Appl. No.: 267,539

[22] Filed: Jun. 29, 1994

Related U.S. Application Data

[63] Continuation of Ser. No. 135,121, Jun. 28, 1993, abandoned, which is a continuation of Ser. No. 830,895, Feb. 4, 1992, abandoned, which is a division of Ser. No. 556,423, Jul. 24, 1990, Pat. No. 5,106,954.

[30] Foreign Application Priority Data

Jul. 26, 1989 [DE] Germany ............... 39 24 746.5

[51] Int. Cl.$^6$ .................. C07K 16/26; C07K 16/24
[52] U.S. Cl. .................. 530/388.23; 424/145.1
[58] Field of Search ............... 530/388.23, 389.2; 435/975; 424/139.1, 145.1, 158.1

[56] References Cited

U.S. PATENT DOCUMENTS

| | | | |
|---|---|---|---|
| 4,474,893 | 10/1984 | Reading | 436/547 |
| 4,558,005 | 12/1985 | Goldwasser et al. | 435/7 |
| 4,558,006 | 12/1985 | Egrie | 435/7 |
| 4,703,008 | 10/1987 | Lin | 435/240.2 |
| 4,722,899 | 2/1988 | Hamaoka et al. | 435/172.2 |
| 4,748,018 | 5/1988 | Stolle et al. | 424/87 |

FOREIGN PATENT DOCUMENTS

| | | |
|---|---|---|
| WO 85/02610 | 6/1985 | WIPO. |
| 86/04068 | 7/1986 | WIPO. |

OTHER PUBLICATIONS

Borrebaeck, Journal of Immunological Methods, vol. 123, pp. 157–165 (1989).
Sytkowski et al., The Journal of Biological Chemistry, vol. 262, No. 3, pp. 1161–1165 (Jan. 25, 1987).
Lee–Huang, Fed. Proc. vol. 41, Abstract No. 1463, p. 520 (1982).
Goto et al., Blood, vol. 74, No. 4, pp. 1415–1423 (Sep. 1989).
Seaver, Genetic Engineering News, pp. 10 and 21 (1994).
Graber et al., Ann Rev. Med. 29:51–66 (1978).
Miyake et al., J. Biol. Chem., 252:5558–5564 (1977).
"Erythropoietin", The Lancet, (1987), pp. 781–782.
Eschbach et al., The New England Journal of Medicine (1987), vol. 316, No. 2, pp. 73–78.
Axen et al., Nature, 214:1302–1304 (1967).
Lai et al., Journal Biol. Chem., vol. 261, No. 7, 1986, pp. 3116–3121.

*Primary Examiner*—Toni R. Scheiner
*Attorney, Agent, or Firm*—Finnegan, Henderson, Farabow, Garrett & Dunner, L.L.P.

[57] ABSTRACT

Erythropoietin (EPO) peptides and the use thereof for preparing epitope-specific anti-EPO antibodies are described. Also described are corresponding anti-EPO antibodies which take the form of polyclonal antibodies (antisera) or of monoclonal antibodies. These antibodies are suitable for purifying EPO, EPO derivatives or EPO peptides. The epitope-specific anti-EPO antibodies according to the invention can also be used for the detection of EPO and, in particular, for the epitope-specific detection of EPO. Additionally described are anti-idiotype antibodies which imitate a receptor region of EPO. Finally, pharmaceuticals which contain the EPO peptides, anti-EPO antibodies or anti-idiotype antibodies, and diagnostic aids for the detection of EPO or of anti-EPO antibodies, are described.

2 Claims, 2 Drawing Sheets

ERYTHROPOIETIN (EPO) PEPTIDES AND ANTIBODIES DIRECTED AGAINST THESE

This application is a continuation of application Ser. No. 08/135,121, filed Jun. 28, 1993, now abandoned, which is a continuation of application Ser. No. 07/830,895, filed Feb. 4, 1992, now abandoned, which is a division of application Ser. No. 07/556,423, filed Jul. 24, 1990, which has been issued as U.S. Pat. No. 5,106,954.

The invention relates to erythropoietin (EPO) peptides and to the use thereof for the preparation of epitope-specific anti-EPO antibodies. The invention furthermore relates to epitope-specific anti-EPO antibodies which may be polyclonal antibodies (antisera) or monoclonal anti-bodies. The invention additionally relates to the use of the epitope-specific anti-EPO antibodies for purifying EPO, EPO derivatives or EPO peptides. The invention also relates to anti-idiotype antibodies which imitate an EPO receptor region. Finally, the invention relates to the use of the epitope-specific anti-EPO antibodies for the detection, preferably the epitope-specific detection, of EPO, pharmaceuticals which contain the said EPO peptides, anti-EPO antibodies or anti-idiotype antibodies and diagnostic aids for the detection of EPO or of anti-EPO antibodies.

Erythropoietin (EPO) is a glycoprotein hormone with 166 amino acids, 4 glycosylation sites on amino-acid positions 24, 38, 83, 126 and a molecular weight of about 34,000. It is initially produced as a precursor protein with a signal peptide of 23 amino acids. EPO stimulates mitotic division and the differentiation of erythrocyte precursor cells and thus ensures the production of erythrocytes. It is produced in the kidney when hypoxic conditions prevail. During EPO-induced differentiation of erythrocyte precursor cells there is induction of globin synthesis and increases in the synthesis of the heme complex and in the number of ferritin receptors. This makes it possible for the cell to take on more iron and synthesize functional hemoglobin. Hemoglobin in mature erythrocytes binds oxygen. Thus, the erythrocytes and the hemoglobin contained in them play a key part in supplying the body with oxygen. The complex processes which have been described are initiated by the interaction of EPO with an appropriate receptor on the cell surface of the erythrocyte precursor cells; cf. Graber and Krantz, Ann. Rev. Med. 29 (1978), 51–66. EPO can either be isolated from natural sources, such as human urine (cf., for example, Miyake et al., J. Biol. Chem. 252 (1977), 5558–5564) or be prepared by genetic engineering methods (cf., for example, EP-A2 148 605).

Patients with renal insufficiency are unable to produce EPO and therefore suffer from anemia. There have already been successful attempts to compensate for this insufficient supply of EPO and to diminish the symptoms of anemia by administering recombinant EPO; cf. The Lancet, Apr. 4, 1987, "Erythropoietin", pages 781–782; Eschbach et al., The New England Journal of Medicine 316 (1987), 73–78. Despite this, little is as yet known about the mechanism of the interaction of EPO with its receptor. However, the use of specific antibodies against EPO would provide the opportunity to establish both the immunological and the functional characteristics of the EPO molecule. Furthermore, disturbances of EPO regulation might be treated with neutralizing antibodies or with EPO peptides binding to the EPO receptor. In this connection, it is advantageous to use EPO peptides rather than to use complete EPO molecules because peptides can be prepared more easily, for example by synthesis.

EPO peptides which correspond to positions 1 to 26, 40 to 59, 80 to 99, 99 to 118, 11 to 129, 131 to 150 and 147 to 166, and antibodies directed against some of these EPO peptides, have already been disclosed by Sytkowski and Donahue, J. Biol. Chem. 262 (1987), 1161–1165. Antibodies which were able to neutralize the biological activity of EPO are prepared by Sytkowski and Donahue only with EPO peptides which correspond to positions 99 to 118 and 111 to 129. The authors conclude from this that the (single) receptor-binding domain is located in the region of amino-acid positions 99 to 129 of EPO. It should be remembered in this connection that the EPO peptides were bonded via glutaraldehyde residues to a carrier for the immunization. EP-A2 148 605 describes, besides the preparation of EPO and derivatives thereof by genetic engineering, EPO peptides which comprise positions 1 to 20, 41 to 57, 116 to 128 and 144 to 166. Polyclonal rabbit antibodies against these EPO peptides are also described; cf. EP-A2 148,605, page 90. However, the antibodies against EPO peptide 116 to 128 do not react with EPO. No neutralizing antibodies or antibodies directed against receptor regions of EPO are described in EP-A2 148,605.

Thus, the technical problem on which the invention is based is to provide novel EPO peptides which allow the determination of further functional and immunological characteristics of EPO. The intention is furthermore to provide novel EPO peptides which bind to the EPO receptor and thus are suitable for treating disturbances of EPO regulation. An additional technical problem on which the invention is based is to provide antibodies against the said EPO peptides which are suitable for the detection of EPO and the treatment of disturbances of EPO function.

The said technical problem is solved by providing the embodiments claimed in the patent claims.

Hence the invention relates to EPO peptides which essentially comprise amino-acid positions 1 to 35 (P4), 7 to 23 (P4/1), 44 to 78 (P3), 52 to 63 (P3/1), 74 to 109 (P1), 84 to 95 (P1/1), 93 to 137 (P5), 110 to 123 (P5/1), 138 to 166 (P2) or 152 to 166 (P2/1) in accordance with the numbering of the amino-acid positions of natural EPO. EPO peptides P1, P1/1, P3 and P3/1 according to the invention are highly immunogenic and allow high-titer epitope-specific anti-EPO antibodies to be prepared. EPO peptides P2 and P2/1 surprisingly allow neutralizing anti-EPO antibodies to be prepared. It is assumed according to the invention that these EPO peptides represent another receptor region which has not previously been identified. Hence these EPO peptides according to the invention are especially suitable for the therapy of disturbances of EPO regulation. EPO peptides P4 and P4/1 are likewise highly immunogenic. By reason of the 100% homology of human EPO with monkey and murine EPO in this region, antibodies against these EPO peptides according to the invention are suitable for more than just the detection of human EPO. EPO peptides P5 and P5/1 according to the invention are suitable for preparing anti-EPO antibodies which can be used to detect natural and partially denatured EPO, for example in Western Blots. These EPO peptides are in the receptor region already described by Sytkowski and Donahue (loc. cit.). The peptides P2, P4 and P5, in particular, are very similar to the corresponding epitopes on the naturally occurring EPO molecule, because specific antibodies reacting with these EPO peptides are suitable for the detection of natural EPO, for example in an ELISA or else in a Western Blot.

The peptides according to the invention can be prepared by chemical or enzymatic cleavage of natural EPO or genetically engineered EPO. They can furthermore be prepared directly by genetic engineering or synthesis. Synthetic preparation is preferred according to the invention.

In preferred embodiments, the EPO peptides P1, P1/1, P3, P3/1, P4, P4/1, P5 or P5/1 according to the invention have the following amino-acid sequences,

| | |
|---|---|
| P1 | VLRGQALLVNSSQPWEPLQLHVDKAVSGLRSLTTLL; |
| P1/1 | SSQPWEPLQLHV; |
| P3 | NEMITVPDTKVNFYAWKRMEVGQQAVEVWQGLALLSEA; |
| P3/1 | KRMEVGQQAVEV; |
| P4 | APPRLICDSRVLERYLLEAKEAENITTGCAEHCSL; |
| P4/1 | CDSRVLERYLLEAKEAE; |
| P5 | LHVDKAVSGLRSLTTLLRALRAQKEAISPPDAASAAPLRTITADT; or |
| P5/1 | FRKLFRRALRAQKEAISPPD. |

In a particularly preferred embodiment, EPO peptides P2 and P2/1 have the following amino-acid sequences:

| | |
|---|---|
| P2 | FRKLFRVYSNFLRGKLKLYTGEACRTGDR; or |
| P2/1 | KLKLYTGEACRTGDR. |

The EPO peptides according to the invention can be used for preparing epitope-specific anti-EPO antibodies. These peptides provide the advantage of a highly pure substance, which can be validated, as immunogen which induces reproducibly defined, high-titer antisera at each immunization.

The EPO peptides according to the invention can be used to prepare both polyclonal epitope-specific anti-EPO antibodies (antisera) and monoclonal epitope-specific anti-EPO antibodies. These antibodies are prepared in a manner known per se. However, according to the invention, the EPO peptides are preferably bound via cysteine residues to a carrier material for the immunization. If the EPO peptides contain no cysteine residue, one is attached in a customary manner.

The invention furthermore relates to the epitope-specific anti-EPO antibodies which can be prepared with the EPO peptides according to the invention. These anti-EPO antibodies are advantageously directed against particular EPO epitopes or EPO domains. This makes it possible to employ them in assay systems in order to carry out epitope-specific detection of normal EPO titers or EPO titers during therapy.

The epitope-specific anti-EPO antibodies according to the invention are either polyclonal antibodies (antisera) or monoclonal antibodies. Since the polyclonal antibodies according to the invention are prepared with the EPO peptides according to the invention, the preparation thereof is reproducible and they are defined and high-titer. They are therefore very particularly suitable for use in all EPO detection systems to be validated.

In another embodiment, the invention relates to anti-idiotype antibodies which are directed against the binding region of the abovementioned anti-EPO antibodies and which imitate an EPO receptor region. These anti-idiotype antibodies bind to the cellular EPO receptor. These anti-idiotype antibodies bare preferably directed against the binding region of anti-P2 or anti-P2/1 antibodies.

In an embodiment which is preferred according to the invention, the epitope-specific anti-EPO antibodies neutralize the biological activity of EPO.

In another preferred embodiment, the abovementioned anti-idiotype antibodies recognize and influence cells which have EPO receptors.

In another embodiment according to the invention, the epitope-specific anti-EPO antibodies according to the invention are used for purifying EPO, EPO derivatives or EPO peptides. The relevant purification processes take the form of customary chromatographic processes, for example immunoadsorption chromatographies or affinity chromatographies. The epitope-specific anti-EPO anti-bodies according to the invention are, where appropriate, bound to carrier materials suitable for chromatography for this purpose.

The invention also relates to the use of the epitope-specific anti-EPO antibodies according to the invention for the detection, preferably the epitope-specific detection, of EPO. The antibodies can also be used for the differential detection of EPO muteins. Such EPO muteins can be modified, for example, in the primary structure, i.e. in their amino-acid sequence. Anti-EPO antibodies which react specifically with such EPO muteins can be prepared using appropriately adapted EPO peptides as have been illustrated hereinbefore. The invention particularly relates to diagnostic aids which contain the EPO peptides, epitope-specific anti-EPO antibodies and/or anti-idiotype antibodies according to the invention.

In another embodiment, the invention relates to pharmaceuticals which contain at least one of the EPO peptides according to the invention or contain epitope-specific anti-EPO antibodies according to the invention. These pharmaceuticals preferably contain EPO peptides which block cellular EPO receptors. In another preferred embodiment, the pharmaceuticals according to the invention contain epitope-specific anti-EPO antibodies according to the invention which neutralize the biological activity of EPO. The pharmaceuticals also contain, where appropriate, pharmaceutically tolerated auxiliaries and additives.

Disturbances of EPO regulation can be treated with the said pharmaceuticals according to the invention.

The figures show:

FIG. 1: Direct erythropoietin-binding assay.

Serum dilutions of epitope-specific or P2/1-specific rabbit antisera were adsorbed onto EPO (20 µg/ml)-coated microtiter plates and bound antibodies were detected with enzyme-labelled anti-rabbit antibodies. Sera 336, 346, 347 and 348 are prepared against the whole EPO molecule, sera 556, 557 and 558 are prepared against the peptide P2, and serum 444 is a rabbit pre-immune serum.

Figure 2:
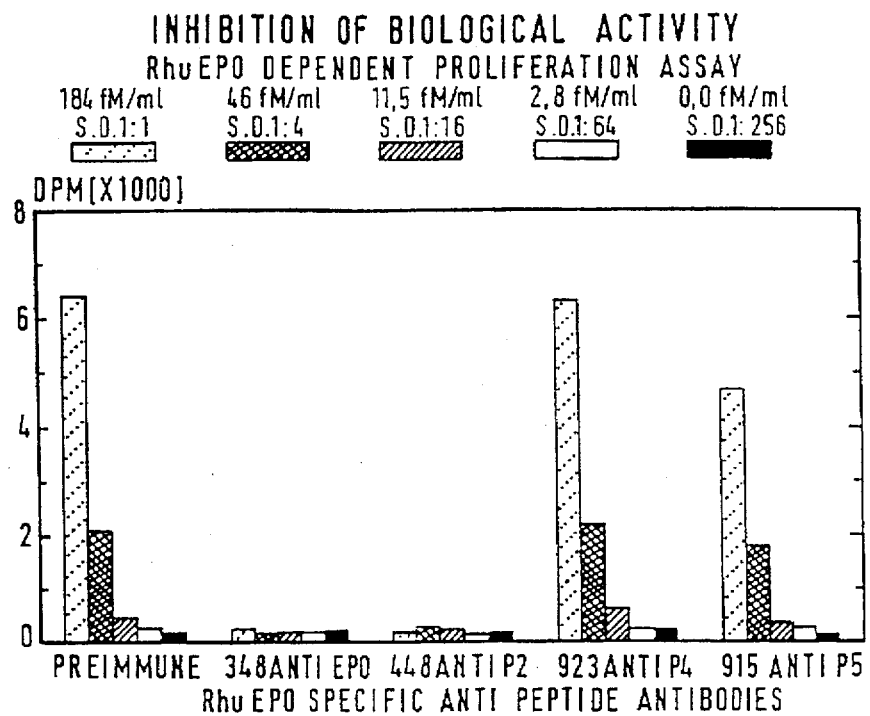

FIG. 2.: Inhibition of the biological activity of recombinant human erythropoietin (rhuEPO) by rhuEPO-specific antisera. Antisera which had been obtained by the immunization of rabbits with rhuEPO or the peptide sequences P2, P4, P5, coupled to keyhole limpet hemocyanin were employed together with rhuEPO in a proliferation test of enriched erythroid precursor cells according to the Krystal method (Exp. Hematol. 7, 649–660). Antibodies which had been obtained by immunization with P2-KLH or EPO-KLH inhibit the proliferation of the erythroid precursor cells induced by rhuEPO.

Figure 3:
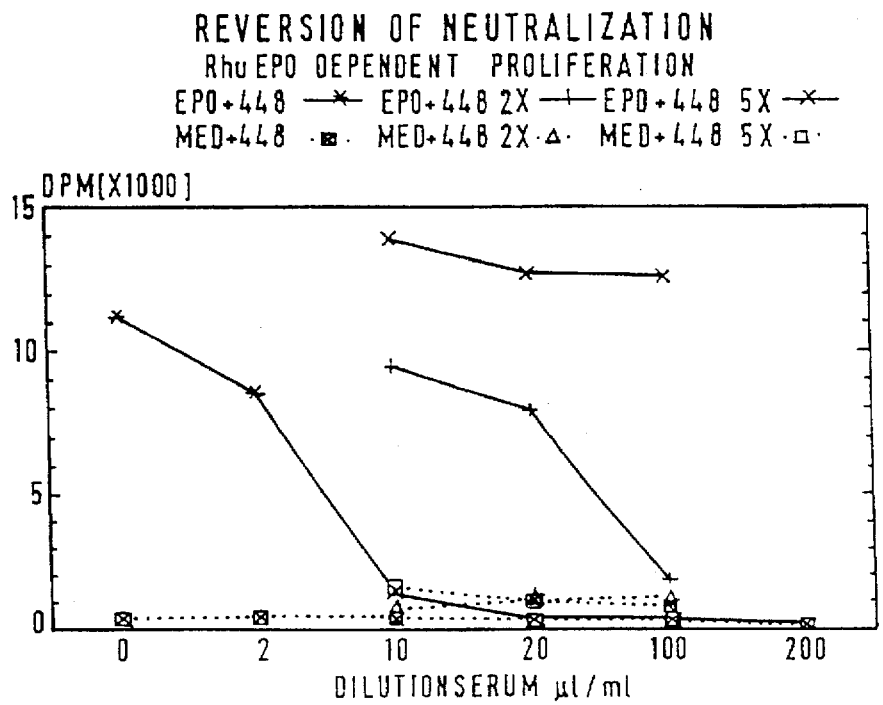

FIG. 3.: Reversal of the inhibition by anti-EPO-P2-KLH sera. The serum was preadsorbed on P2-SEPHAROSE resin up to 5 times before the incubation of the precursor cells with rhuEPO and anti-P2-KLH antiserum in the Krystal assay (see above). The inhibitory activity of the serum can be removed completely by the preadsorption on peptide P2.

Material and methods
Preparation of the peptides

The peptides were preferably prepared by the solid-phase method on a polystyrene matrix (1% crosslinked with divinylbenzene). The loading of the polystyrene matrix with functional groups (—NH₂) was preferably 0.4–0.6 mmol/g of matrix. Since the peptides were prepared using the base-labile Fmoc group, p-alkoxybenzyl esters were used as anchor molecules. In general, dichloromethane and dimethylformamide were used during the synthesis, N-methylpyrrolidone in exceptional cases. The amounts of the wash or reaction liquids were preferably about 15 ml. Since the alpha-NH₂ groups of the amino acids were protected with the Fmoc group, the following protective groups were chosen for the side groups of the trifunctional amino acids:

| Serine, threonine, tyrosine | tert.-butyl ethers |
|---|---|
| Glutamic acid, aspartic acid | tert.-butyl esters |
| Arginine | 4-methoxy-2,3,6-trimethylphenyl-sulfonyl |
| Cysteine | tert.-butylmercapto |
| Lysine | tert.-butyloxycarbonyl |

The amino acids were preferably coupled via active esters, and in situ activation by HOBt/diisopropylcarbodiimide was particularly preferred.

The repetitive alpha-NH₂ protective group elimination was carried out with a base, preferably with 20% piperidine in DMF at room temperature.

The resin was washed with DMF and isopropyl alcohol after each of these reactions steps, coupling or deblocking. Acidolysis resulted in simultaneous elimination of the protective groups from the side groups and of the peptides from the matrix. This was preferably carried out using a mixture of trifluoroacetic acid and ethanedithiol (9:1, v/v). The sulfhydryl group of the cysteines was liberated by substances containing mercapto groups, such as, for example, dithiothreitol or butylphosphine.

The synthetic peptides were investigated for their chemical composition and their purity. The composition of the peptides was determined by amino-acid analysis. For this purpose, a small sample was hydrolyzed with 6N hydrochloric acid in the presence of phenol at 110° C. for 24 or 72 hours, and the individual amino acids were determined quantitatively. The peptide contents were about 85%. The peptides were purified where appropriate by RP-HPLC (reversed phase high performance liquid chromatography) by known methods. The purity of the peptides was determined by HPLC on C18 reversed phase columns. A phosphate/acetonitrile gradient was used for this purpose, and a purity of more than 85% was found.

Coupling of the peptides to carrier molecules

The peptides were preferably coupled via cysteine residues to a high molecular weight carrier protein, for example to albumin or ovalbumin, preferably to keyhole limpet hemocyanin (KLH). The coupling was effected via a thio-ether linkage to the mercapto group of the cysteine. This type of coupling has the advantage that the peptide is coupled in a defined way to the carrier protein. If the peptides contained no cysteine residue, a cysteine residue was attached.

Coupling of the peptides to SEPHAROSE resins

The peptides were coupled to SEPHAROSE resins by a standard process using SEPHAROSE resins activated with cyanogen bromide.

Preparation of the antisera
Immunization of rabbits

In order to produce antibodies specific for EPO peptides, the peptide-KLH conjugates were emulsified with adjuvants and injected into rabbits in accordance with a 5-week immunization regimen. After this time the animals had produced specific antibodies and were bled.

Detection of specific antibodies

A solid-phase ELISA was used to assay the sera for peptide or EPO specificity. The content of peptide-specific and EPO-specific antibodies in the antisera or in the antibody fractions which had been purified by affinity chromatography was determined in plastic microtiter plates, which were coated with purified EPO or with EPO peptides, using an enzyme-coupled anti-rabbit-Ig antiserum. In parallel with this, the antibodies were examined in a Western Blot to detect the specific EPO bands of 34–38 kDa.

Determination of neutralizing antibodies

The Krystal proliferation test (1983, Exp. Hematol. 7, 649–660) was used to examine the rhuEPO-specific or rhuEPO peptide-specific antisera for neutralizing properties. Female NMRI mice were injected with 48 mg/kg phenylhydrazine hypochloride on two consecutive days. 48 hours after the last injection the spleens of the animals were removed, and a single cell suspension was prepared. Erythroid precursor cells were enriched by means of a Ficol-gradient (D=1.077). In order to induce the proliferation of the cells, $3 \times 10^5$ cells/well were incubated with 0.1 pmol/ml rhuEPO in a 96-well microtiter plate. In order to carry out the inhibition tests, EPO was pre-incubated with dilutions of the antisera and then used in the proliferation test.

Epitope-specific antibodies were purified by standard methods, the antibodies being adsorbed onto the SEPHAROSE resins overnight from an ammonium sulfate precipitate which had been dialyzed against PBS, unbound material being washed out with PBS, pH 7.0, and subsequently the specific antibodies being eluted with aqueous acid, pH 2.5. The eluates were immediately neutralized to pH 7.0 with solid sodium phosphate and dialyzed against PBS.

Coupling of epitope-specific antibodies to SEPHAROSE resins

The epitope-specific antibodies were coupled in a standard process to SEPHAROSE resins activated with cyanogen bromide.

Purification of erythropoietin by affinity chromatography

Erythropoietin from cell culture supernatants was adsorbed onto epitope-specific antibody columns and could be eluted, without loss of biological activity, by customary processes by changing the pH from pH 7–8 to pH 2–3.

The examples illustrate the invention. The following abbreviations are used in these:

| t-Bu | tert.-butyl ether |
|---|---|
| Mtr | 4-methoxy-2,3,6-trimethylphenylsulfonyl |
| DMF | dimethylformamide |
| HOBt | hydroxybenzotriazole |
| Boc | tert.-butyloxycarbonyl |
| Fmoc | fluorenylmethoxycarbonyl |
| GMBS | gamma-maleimidobutyric acid N-hydroxysuccinimide ester |

EXAMPLE 1

Preparation of the immunizing antigen a) Synthesis of peptide (P2/1):

H-Lys-Leu-Lys-Leu-Tyr-Thr-Gly-Glu-Ala-Cys-Arg-Thr-Gly-Asp-Arg

The peptide was synthesized using a completely automatic peptide synthesizer. The protective groups were eliminated from 1 g of Fmoc-Arg(Mtr)-p-alkoxybenzyl-ester-resin with 15 ml of 20% piperidine/DMF (v/v), followed by washing several times with DMF and isopropanol. 1 mmol of Fmoc-Asp(t-Bu) (three-fold excess) and 203 mg of HOBt dissolved in 15 ml of DMF were added. After addition of 1.1 ml of a 1M diisopropylcarbodiimide solution (dichloromethane), the coupling was carried out for 1.5 hours. Excess reagents were removed by washing with DMF in isopropanol. This coupling scheme was maintained up to the N-terminal amino acid. A Boc-protected amino acid was employed as the final amino acid. Each coupling step was checked for completeness by a ninhydrin test. 1.06 g of resin were stirred with 2.5 ml of thioanisole, 2.5 ml of ethanedithiol and 15 ml of trifluoroacetic acid at 35° C. for 4 hours and filtered off. The acid solution was poured into ether, and the precipitated peptide was filtered off and chromatographed on a SEPHADEX G25 column, 3×100 cm, 0.5% acetic acid. The peptide pool was freeze dried. The yield was 230 mg.

b) Liberation of the sulfhydryl group 70 mg of the peptide were dissolved in 7 ml of trifluoroethanol and 350 µl of water, and the pH was adjusted to 7.3 with N-methylmorpholine. The reaction vessel was flushed with nitrogen, and 40 µl of tri-n-butylphosphine were added. The mixture was stirred at room temperature for 1 hour, diluted with 50 ml of water and the pH was adjusted to 4.0. The aqueous phase was extracted three times with 10 ml of diethyl ether, concentrated to 10 ml and purified on SEPHADEX G25 (3×100 cm; 0.5% acetic acid). 55 mg of peptide were obtained after freeze drying.

c) Conjugate preparation 30 mg of KLH (keyhole limpet hemocyanin) were dissolved in 0.05 mmol/l sodium phosphate buffer, pH 8.0, and activated with 3 mg of GBMS for 1 hour. The protein was chromatographed on a SEPHADEX G50 column (2×30 cm) (0.1 mol/l sodium phosphate; 0.5 mmol/l EDTA, pH 6.0). The protein pool was concentrated to 6 ml and incubated with 30 mg of the peptide containing sulfhydryl groups for 1 hour. Dialysis and freeze drying resulted in 38 mg of peptide conjugate.

EXAMPLE 2

Immunization of rabbits

Rabbits were immunized with 1.7 mg of antigen per animal on each occasion for a period of 5 weeks. At the first immunization, the animals each received 0.4 mg of antigen in complete Freund's adjuvant (CFA) subcutaneously at 8 immunization sites in the vicinity of the lymph nodes. This was followed 2 weeks later by subcutaneous immunization with 0.8 mg of antigen/animal in CFA. After a further 2 weeks, the animals received intravenous administration of 0.1 mg of antigen in Aerosil on each of 5 consecutive days. 3 days later they were bled, and the individual antisera were obtained.

EXAMPLE 3

Preparation of immunoadsorbants with peptides

For the purification of the crude antisera by affinity chromatography, about 20 mg of, for example, the pentadecapeptide (P2/1):

H-Lys-Leu-Lys-Leu-Tyr-Thr-Gly-Glu-Ala-Cys-Arg-Thr-Gly-Asp-Arg-OH were immobilized covalently on a solid phase. The coupling reaction was carried out with SEPHAROSE resins activated with cyanogen bromide by a described process (Axen et al., Nature 214 (1967), 1302). The immunoadsorbant was subsequently washed in each case with phosphate-buffered saline (PBS; 0.15 mol/l, pH 7.2) and acetic acid (0.5 mol/l, pH 2.5). Before use, the adsorbent was equilibrated with three times the volume of PBS. Yield: about 20 ml of peptide-SEPHAROSE resins.

The other peptides were used in the same way for preparing immunoadsorbants.

EXAMPLE 4

Obtaining antibodies 100 ml of crude antiserum were applied to a PBS-equilibrated peptide-SEPHAROSE (1.5×15 cm) and subsequently washed with PBS until the extinction at 280 nm was 0.01. This was followed by washing steps with 1M NaCl, pH 7.0, and water (pH 7.0), using 3 times the gel volume in each case. The antibodies were eluted from the immunoadsorbant with water (pH 2.5), and the antibody solution was adjusted to pH 7.0 with solid sodium phosphate (0.001 mol/l), concentrated (Amicon membrane) and stored at −70° C. Yield: 35 mg of antibody.

EXAMPLE 5

Testing of the antibodies a) Preparation of EPO- or peptide-coated microtiter plates 20 µg/ml EPO or EPO-specific peptides were coupled in carbonate buffer in plastic microtiter plates at 4° C. overnight. Before carrying out the assays, the plates were washed twice with PBS, saturated with PBS/0.5% BSA for 30 minutes and then washed three times with PBS.

b) Enzyme immunoassay procedure

The plates saturated with BSA were incubated with dilutions of the anti-EPO rabbit antisera or of the purified antibody fractions for 2 hours. After this time they were washed with PBS and incubated with anti-rabbit Ig antiserum, which was coupled to alkaline phosphatase, for 2 hours. This was followed by two washes with PBS, then two with 0.2M tris-HCl, pH 9.5, and then briefly with 1M tris-HCl, pH 9.5. The reaction was stopped with 1M NaOH after one hour, and the optical density at 405 mm was measured.

c) Western Blot procedure

EPO standards were fractionated by polyacrylamide gel electrophoresis and transferred to nitrocellulose (Towbin et al., Proc. Natl. Acad. Sci. USA, 76 (1979), 4350–4354). The filters were saturated in PBS/0.5% BSA and then incubated with the antibodies overnight. The filters were then washed three times with PBS and incubated with anti-rabbit Ig antiserum conjugated to alkaline phosphatase, for 2 hours. Three washes in PBS, one wash in 0.2M tris-HCl, pH 9.5, and a brief wash in 1M tris-HCl, pH 9.5, were followed by development of the blots with 4-nitrotetrazoliumchloride blue hydrate (500 µg/ml) and 5-bromo-4-chloro-indoxyl phosphate p-toluidinium salt (200 µg/ml) in 1M tris-HCl, pH 9.5. The reaction was stopped with water after 20 minutes.

EXAMPLE 6

Preparation of immunoadsorbants with antibodies 20 to 50 mg of antibodies purified by affinity chromatography were coupled by a standard process (Axen et al., Nature 214 (1967), 1302) to SEPHAROSE resins activated with cyanogen bromide and further treated as described in Example 3.

EXAMPLE 7

Purification of erythropoietin by affinity chromatography

Immunoadsorbants which contained EPO-specific antibodies were employed as described above for the purification of EPO and EPO muteins by affinity chromatography.

EXAMPLE 8

Preparation of monoclonal antibodies

For the preparation of monoclonal antibodies, EPO obtained by recombinant DNA techniques and also the peptides described above were used as antigens. The peptides were coupled to KLH (keyhole limpet hemocyanin) beforehand.

Balb/c mice (female) were immunized intraperitoneally or subcutaneously with 10 μg and were boosted for several weeks. Immediately before the actual fusion, the experimental animals were additionally boosted intravenously for 4 consecutive days.

On the day of the fusion the spleens were removed sterile and suspended to give single cells. By means of the fusion of $10^8$ spleen cells with $2 \times 10^7$ cells of a myeloma cell line (SP 2/0), hybrid cells were created which were subsequently distributed in a concentration of $10^6$ cells/well in a selective medium (DMEM (Dulbecco's minimal essential medium)+ 20% FCS (fetal calf serum); 0.1 mM hypoxanthine; 0.4 mM aminopterin; 16 mM thymidine) on 24-well plates (Costar). After 2–3 weeks single cell colonies were isolated from the wells and transferred to another well in new culture plates (24-well, Costar) in each case. After a further 2–3 days, these culture supernatants were screened for the presence of anti-EPO antibodies in an enzyme immunoassay. Hybrids producing specific antibodies were selected and were cloned with the aid of a single cell manipulator.

EXAMPLE 9

Preparation and determination of anti-idiotypic antibodies

A syngenic monoclonal antibody with the desired specificity against EPO/EPO peptide was used for the immunization. Instead of the entire antibody, the Fab'-fragment was coupled to BSA or KLH and was injected intraperitoneally or subcutaneously in CFA (complete Freund's adjuvant) into female Balb/c mice. The further preparation of the monoclonal anti-idiotypic antibodies corresponds to the process described in Example 8.

Culture supernatants were tested for the presence of anti-idiotype antibodies in an enzyme immunoassay using the antibody employed in the immunization conjugated to peroxidase (POD), and in yet another enzyme immunoassay it was tested whether these anti-idiotype antibodies can be inhibited by antigens. Hybrids producing anti-idiotype antibodies which can be inhibited by antigens were selected and were cloned with the aid of a single cell manipulator.

We claim:

1. A monoclonal antibody directed against an erythropoietin (EPO) peptide, wherein said antibody neutralizes the biological activity of EPO, and wherein said EPO peptide consists essentially of a peptide of less than the complete erythropoietin protein, said peptide having an amino acid sequence consisting of amino acid positions 138 to 166 (P2) in accordance with the numbering of the amino acid positions of natural EPO.

2. A monoclonal antibody directed against an erythropoietin (EPO) peptide, wherein said antibody neutralizes the biological activity of EPO, and wherein said EPO peptide consists essentially of a peptide of less than the complete erythropoietin protein, said peptide having an amino acid sequence consisting of amino acid positions 152 to 166 (P2/1) in accordance with the numbering of the amino acid positions of natural EPO.

* * * * *